United States Patent [19]
Stokes et al.

[11] Patent Number: 5,932,563
[45] Date of Patent: Aug. 3, 1999

[54] METHODS FOR TREATING SPINAL CORD INJURY

[75] Inventors: Bradford T. Stokes, Worthington; Phillip G. Popovich, Columbus, both of Ohio; Nico Van Rooijen, Haarlem; Inge Huitinga, Amsterdam, both of Netherlands

[73] Assignee: Ohio State Research Foundation, Columbus, Ohio

[21] Appl. No.: 09/177,948

[22] Filed: Oct. 23, 1998

[51] Int. Cl.⁶ ........................................... A61K 31/66
[52] U.S. Cl. ................................................ 514/108
[58] Field of Search ................................. 514/108

[56] References Cited

U.S. PATENT DOCUMENTS

| | | | |
|---|---|---|---|
| 4,009,270 | 2/1977 | Gainer, Jr. | 424/195 |
| 5,030,656 | 7/1991 | O'Brien et al. | 514/523 |
| 5,189,018 | 2/1993 | Goldman et al. | 514/10 |
| 5,360,797 | 11/1994 | Johnson et al. | 514/111 |
| 5,662,918 | 9/1997 | Winter et al. | 424/423 |

OTHER PUBLICATIONS

"Effects of silica on the outcome from experimental spinal cord injury: implication of microphages in secondary tissue damage" by Blight, AR, *Neuroscience*, 60:263–273, 1994.
"Liposome–mediated monocyte depletion during wallerian degeneration defines the role of hematogenous phagocytes in myelin removal" by Bruck, et al., *J. Neurosci. Res.* 46: 477–484, 1996.
"Inhibition of mononuclear phagocytes reduces ischemic injury in the spinal cord" by Giulian, et al., *Ann Neurol.* 227: 33–42, 1990.
"Liposome mediaated affection of monocytes" by Huitinga, et al., *Immunobiology*, 185: 11–19, 1992.
"Liposome mediated depletion of macrophages: mechanism of action, preparation of liposomes and applications" by van Rooijen, et al., *J. Immunol. Methods*, 174: 83–93, 1994.
"Impantation of stimulated homologous macrophages results in partial recovery of paraplegic rats" by Rapalino, et al., *Nature Medicine*, vol. 4 No. 7, Jul. 1998, pp. 814–821.
"Methylprednisolone inhibits early inflammatory processes but not ischemic cell death after experimental spinal cord lesion in the rat" by Barhodi, et al., *Brain Researh* 672, 1995, pp. 177–186.

"Phagoctyic Response in Photochemically Induced Infarction of Rat Cerebral Cortex" by Schroeter, et al., *Stroke*, vol. 28 No. 2, Feb. 1997, pp. 382–386.
"Suppression of Experimental Allergic Encephalomyelitis in Lewis Rats After Elimination of Macrophages" by Huitinga, et al., *J. Exp. Med.*, vol.. 172, Oct. 1990, pp. 1025–1033.
"Quinolinic acid accumulation and functional deficits following experimental spinal cord injury" by Blight, et al., *Brain*, 118, 1995, pp. 735–752.
"The Role of Macrophages, Perivascular Cells, and Microglial Cells in the Pathogenesis of Experimental Autoimmune Encephalomyelitis" by Bauer, et al. *GLIA*, 15:437–446 (1995).
"Cellular Inflammatory Response After Spinal Cord Injury in Sprague–Dawley and Lewis Rats" by Popovich,, et al., *The Journal of Comparative Neurology*, 377:443–464 (1997).
"Apoptosis of macrophages induced by liposome–mediated intracellular delivery of clodronate and propamidine" by van Rooijen, et al., *Journal of Immunological Methods*, 193 (1996) pp. 93–99.
Abstract 155, "Circulating Macrophages as Pathological Effector Cells after Spinal Cord Injury" by Popovich, et al., Abstracts of the International Society for Neuroimmunology Fifth International Congress, Montreal, Canada, Aug. 23–27, 1998.
Abstract 130, "Selective Depletion of Peripheral Macrophages Attenuates Myelin Loss and Improves Hindlimb Function in Spinal Injures Rats" by Popovich, et al., *Journal of Neurotrauma*, vol. 14, No. 10, Oct. 1997.

*Primary Examiner*—Raymond Henley, III
*Attorney, Agent, or Firm*—Calfee, Halter & Griswold LLP

[57] ABSTRACT

New methods for treating patients with a traumatic contusion-type spinal cord injury are provided. The method comprises the steps of providing a patient having a contusion-type injury and administering liposomes containing dichloromethylene diphosphonate (hereinafter referred to as "$Cl_2MBP$") . The liposomes are preferably administered to the patient by intravenous injection. The liposomes are administered prior to the onset of infiltration of the spinal cord by the peripheral macrophages. Preferably, the liposomes are administered to the patient multiple times preferably during a period extending from 0 hours to seven days after occurrence of the injury. In a preferred embodiment, the liposomes are multilamellar phosphatidylcholine liposomes.

7 Claims, No Drawings

METHODS FOR TREATING SPINAL CORD INJURY

The present invention was made with support from National Institutes of Health Grant No. T32-NS07291-05 and Grant No. NS33696. The United States Government has certain rights in the invention.

BACKGROUND

Approximately 7800 spinal cord injuries occur in the United States each year. Motor vehicle accidents are the leading cause of spinal cord injury, followed by acts of violence, falls, and sports. The majority of injuries occur at the mid-cervical and upper thoracic regions of the spinal cord.

Approximately 45% of the injuries result in total or complete loss of sensation and function below the level of injury. The remaining 55% of the injuries result in partial loss of sensation and function below the level of injury. Such injuries are incomplete. In incomplete spinal cord injuries, the primary traumatic injury can destroy as much as 90% of the axons in the spinal cord. However, such patients can still recover substantial function as a result of the axons that are spared at the injury site.

The primary trauma to the spinal cord causes a central hemorrhagic necrosis. The central part of the spinal cord, i.e., the gray matter dies first. Generally a rim of white matter containing myelinated axons is preserved. Following the initial injury, a series of degenerative processes which promote tissue damage beyond the original site of injury are initiated. This is referred to as secondary injury.

At present, the only method which has currently been shown to be effective at reducing or minimizing the damage resulting from this secondary injury is intravenous injection of the glucocorticoid methylprednisolone. Methylprednisolone is a potent free radical scavenger which may also serve to reduce inflammation of the central nervous system. Methylprednisolone is administered to the patient in high doses (30 mg/kg body weight) shortly after injury, typically within the first 8 hours. Unfortunately, prolonged administration of glucocorticoids has adverse systemic effects (e.g. increased incidence of sepsis and pneumonia) and is limited in its therapeutic window.

Accordingly, it is desirable to have additional methods for treating spinal cord injury, particularly the secondary spinal cord injury that results from trauma. A treatment which can be employed at a time which is more than 8 hours after occurrence of the initial injury is especially desirable.

SUMMARY OF THE INVENTION

New methods for treating patients with a traumatic contusion-type spinal cord injury are provided. The method comprises the steps of providing a patient having a contusion-type injury and administering liposomes containing dichloromethylene diphosphonate (hereinafter referred to as "$Cl_2MBP$"). The liposomes are preferably administered to the patient by intravenous injection. The liposomes are administered prior to the onset of infiltration of the spinal cord by the peripheral macrophages. Preferably, the liposomes are administered to the patient multiple times preferably during a period extending from 0 hours to seven days after occurrence of the injury. In a preferred embodiment, the liposomes are multilamellar phosphatidylcholine liposomes.

DETAILED DESCRIPTION OF THE INVENTION

A new method for treating patients with traumatic contusion-type spinal cord injuries is provided. The patient is a mammalian patient. The method comprises the steps of providing a patient having a contusion-type injury and administering liposomes containing $Cl_2MBP$. It is believed that such treatment causes selective destruction of peripheral blood-derived macrophages in the patient with concomitant sparing of the resident microglial cells, which are located in the spinal cord.

LIPOSOMES

The liposomes are multilamellar liposomes which are capable of being phagocytized by macrophages. Such liposomes are prepared by conventional techniques. Suitable lipids include for example, phosphatidylcholine, phosphatidylserine, phosphatidylglycerol, cardiolipin, cholesterol, phosphatidic acid, sphingolipids, glycolipids, fatty acids, sterols, phosphatidylethanolamine, polymerizable phospholipids both in their polymerized and nonpolymerized states, and mixtures thereof. . Preferably, the liposomes are less than 6 microns in diameter, more preferably about 1 micron in diameter.

Multilamellar liposomes were prepared as described in van Rooijen, N. 1989. The liposome-mediated macrophage 'suicide' technique. J. Immunol. Methods 124: 1–6, which is specifically incorporated herein by reference. To prepare the liposomes, 86 mg phosphatidylcholine and 8 mg cholesterol from Sigma, St. Louis, Mo. were dissolved in 10 ml chloroform in a 500 ml round bottom flask then dried in vacuo on a rotary evaporator to form a film. The total amount of lipids in the film was 140 mmols. The molar ratio of phosphatidylcholine/cholesterol was 6:1. To incorporate $Cl_2MBP$ into the liposomes, 10 ml of a phosphate buffered saline (PBS) solution containing $Cl_2MBP$ was added to the dried film, and the bottom flask was rotated until the lipid film was dispersed into liposomes. The PBS solution was prepared by adding 2.5 g $Cl_2MBP$ to 10 ml of PBS (0.15M NaCl in 10 mM phosphate buffer, pH 7.4). $Cl_2MBP$ was a gift from Boehringer Mannheim GmbH, Mannheim, Germany. The resulting liposome preparations were kept at room temperature for 2 hours, sonicated for 3 minutes at 20° C. (50 Hz), then kept at room temperature for another 2 hours. The liposomes were centrifuged at 100,000×g for 30 minutes and resuspended in 4 ml PBS.

ADMINISTRATION OF LIPOSOMES

The liposomes are administered in suspension. The lipid concentrations of the suspensions can be in the 1–1000 mg/ml range, preferably in the 50 to 400 mg/ml range. Preferably, the liposomal suspensions are administered by intravenous injection.

The liposomes are administered to the patient prior to the onset of infiltration of the peripheral macrophages into the patient's spinal cord. The liposomes are administered to the patient at least once during a time period extending from 0 hours to 7 days after occurrence of the injury. Preferably, the liposomes are administered to the patient multiple times during the period extending from 0 hours to 7 days after occurrence of the injury. Advantageously, the liposomes may be administered to the patient more than 8 hours after occurrence of the injury. Good results have been obtained when liposomes containing $Cl_2MBP$ were injected into rats having a contusion-type spinal cord injury at 24 hours (i.e. 1 day), 3 days and 6 days after occurrence of the injury.

Production of Injury

"Contusion type injury" was obtained in rats by displacement of the spinal cord. The anesthetized rats received a partial laminectomy of the 8th thoracic vertebrae after which the spinal cord was displaced a distance of 0.9 mm over 23 msec using the Ohio State spinal contusion injury device as described in Stokes B. T., Noyes D. H., Behrmann D. L. (1992) An electromechanical spinal injury device with dynamic sensitivity. J. Neurotrauma 9:187–195. Postoperative care consisted of hydration with lactated Ringer's solution (5 cc, s.q.), manual voiding of bladders 2–3 times/day, and daily injection of antibiotics (s.q., gentamycin, 1 mg/kg). On days of behavioral evaluation, injections were given after testing was completed. Injured rats survived either 7 or 28 days post-injury.

EXAMPLE 1

A total of 22 female Lewis rats having a contusion type injury of the spinal cord were injected with multilamellar liposomes containing $Cl_2MBP$ at days 1, 3, and 6 post-injury into the tail vein. A 2 ml suspension of $Cl_2MBP$-liposomes was injected into the tail vein of the rats at days 1, 3, and 6 post-injury. There were no adverse side effects associated with any of the injection schedules.

Controls

Twenty-two rats having a contusion type injury generated as described above were injected with a 2 ml suspension of PBS liposomes on 1, 3, and 6 days post-injury. The PBS liposomes, which contained PBS but lacked $Cl_2MBP$, were prepared as described above in Example 1. Twelve rats having a contusion type injury were injected with a 2 ml of PBS on 1, 3, and 6 days post-injury. Eight rats having a contusion-type injury received no post-injury treatment.

Behavioral Evaluation.

The ability of the control rats and the rats treated with $Cl_2MBP$ containing liposomes to recover hindlimb movement was assessed using the standardized Basso-Beattie-Bresnahan (BBB) locomotor rating scale as described in Basso D M, Beattie M S, Bresnahan J C (1995) A sensitive and reliable locomotor rating scale for open field testing in rats. 12:1–21. The BBB analysis was supplemented with a subscoring system to assess changes in locomotor parameters that may not be coupled to FL/HL coordination. A subscore, 0–5, was given to each hindlimb based on paw rotation and toe clearance of the hindlimb. Sub-scores were assigned as follows: paw position, 0=rotation at initial contact and liftoff, 1=rotation at initial contact or liftoff and parallel at initial contact/liftoff, 2=parallel at initial contact and liftoff; toe clearance, 0=no clearance, 1=occasional clearance (£ 50% of the time), 2=frequent clearance (51–95%), 3=consistent (>95%) clearance. The cumulative scores of each hindlimb were summed to yield a single score (maximum score of 10/rat). Open field locomotor scores were analyzed by repeated measures analysis of variance with Tukey's multiple comparison test at each time point. Behavioral subscores were analyzed using the Mann-Whitney nonparametric test.

Injured rats were tested daily for one week at which time one-half of the animals in each group were randomly selected and euthanized via intracardiac perfusion with 4% paraformaldehyde. The remaining animals were tested on days 10, 14, 18, 21, 24, and 28 post-injury. All remaining animals were euthanized after testing on day 28.

Results

Pronounced hindlimb impairment was observed immediately after spinal cord injury with partial recovery over the next four weeks in the $Cl_2MBP$-treated and control animals. Typical recovery patterns in $Cl_2MBP$-treated animals and control. animals progressed from flaccid hindlimb paralysis on days 1 and 3 post-injury to frequent or consistent plantar stepping by four weeks post-injury. Motor deficits were still apparent at this chronic post-injury time point and included paw rotation, inability to clear the toe during the swing phase of stepping and hindlimbs that were widely abducted. The severity of these deficits was much greater in animals treated with the PBS liposomes than in animals treated with the liposomes containing $Cl_2MBP$ as described in example 1.

Animals treated with $Cl_2MBP$-containing liposomes as described in example 1 were able to position their paw parallel to the body and/or clear their toes during the step cycle. External paw rotation/hindlimb abduction without toe clearance was observed in only 6 $Cl_2MBP$-treated animals (38%) compared to 14 control animals (61%). Of the control animals that had a subscore >0, a third of these animals never cleared their toes during the step cycle. Only 1 $Cl_2MBP$-treated animal showed this deficit. The characteristics of hindlimb use exhibited by the $Cl_2MBP$-treated animals are typical of normal uninjured rats. Further improvement in locomotion was evident in 31% of $Cl_2MBP$-treated animals with 3 achieving frequent and 1 animal recovering consistent coordination. Only 1 out of 14 control rats showed frequent coordinated forelimb hindlimb stepping by 4 weeks post-injury.

Macrophage and Axon Analysis.

The spinal cords of the control and treated animals were removed and placed in fixative. Using the impact site as the central point, a 14 mm segment of each injured spinal cord was embedded in paraffin. The remainder of the spinal tissue rostral and caudal to the injury site was immersed in 30% sucrose then frozen on dry ice. Paraffin blocks were serially sectioned at 15 m in the transverse plane with every $4^{th}$, $5^{th}$, and $6^{th}$ sections kept for morphometric analysis.

Paraffin sections adjacent to those used for morphometric analysis were used for immunohistochemical detection of macrophages using ED1 antibody (1:1,000) from Harlan Bioproducts for Sciencespecific. ED1 antibody is specific for a cytoplasmic protein with homology to the CD68 molecule in phagocytic macrophages. Axons were immunolabeled with RT-97 antibody (1:1,500) from Boehringer Mannheim. RT-97 antibody is specific for the 200 kd phosphorylated neurofilaments in large caliber axons. Paraffin embedded tissues were de-waxed through xylene then rehydrated through descending concentrations of alcohol (100%–70%) into PBS. Rehydrated tissues were incubated with primary antibodies then visualized using a modified immunoperoxidase technique.

Macrophage activation/infiltration was quantified using proportional area measurements as defined in Popovich P G, Wei P, Stokes B T (1997) Cellular inflammatory response after spinal cord injury in Sprague-Dawley and Lewis rats. J Comp Neurol 377:443–464. Briefly, an increased proportional area value (area fraction of tissue occupied by immunohistochemically stained macrophages relative to the area of the region sampled) indicates an increase in macrophage size or cell density. To quantify macrophages in white matter, LFB-stained tissues were used to create a template after which the digital templates were superimposed onto adjacent ED1-stained tissue sections. Macrophages were also quantified within the central region of the spinal cord that was circumscribed by the white matter templates. Within these central regions, no attempts were made to distinguish between macrophages in cavities, regions of spared gray matter or fibrous connective tissue. RT-97 positive axons were quantified in an identical fashion. For axon quantification, these different types of analyses estimated the degree of axon sparing, regeneration, and/or sprouting within the center of the lesion and in spinal white matter, respectively.

Livers and spleens were removed, placed in fixative, embedded in paraffin and sectioned. Thereafter the liver and spleen sections were stained with ED1. The results confirmed peripheral macrophage depletion in the $Cl_2MBP$-treated animals.

Results

In the spinal tissue of the $Cl_2MBP$-treated animals, significant depletion of macrophages was evident within regions previously occupied by gray matter (central spinal cord). ED1+ macrophages, presumably activated microglia, were still present in the white matter, although there was a tendency for fewer ED1+ cells to be present in these spinal regions by 28 days post-injury. Remnants of gray matter and the accumulation of a cellular matrix were present in the chronically injured spinal cord of the $Cl_2MBP$-treated rats.

Microscopic analysis of injured spinal cord sections also revealed a well-developed fibrous matrix and remnants of gray matter within the lesion epicenter of the $Cl_2MBP$-treated animals. The matrix is presumably comprised of glia, fibroblasts, ependyma, and endothelial cells.

Neurofilament immunohistochemistry revealed few axons within the lesion center or white matter of control animals. In contrast, robust sprouting and/or axonal regeneration was co-localized to regions of cellular matrix accumulation in the spinal cord of the $Cl_2MBP$-treated animals. These axons appeared to grow without specific orientation and often surrounded blood vessels. A significant sparing of large caliber axons was also observed within the spared white matter of the $Cl_2MBP$-treated animals.

Morphometric Analysis of the Contusion Lesion.

Myelin sparing of luxol fast blue (LFB)-stained tissue sections was assessed over an 8 mm rostral-caudal interval of the contusion lesion using computer-assisted morphometric techniques (MCID, Imaging Research, Inc., Ontario, Canada). Cresyl violet counterstains were used to facilitate identification of cell nuclei and to discriminate between cellular debris and intact/preserved tissue. Spared white matter was quantified by measuring the area of tissue identified by LFB-positive tissue. Computer-defined regions of LFB staining were always confirmed and when necessary, manually edited using high power light microscopy (50×). This type of analysis has been shown to correlate with locomotor recovery and is a preferred method for assessing the efficacy of various pharmacotherapies after rodent spinal cord injury. Areas devoid of tissue or tissue containing only cellular debris or macrophages were designated as areas of cavitation. Often times spared gray matter or a fibrous connective tissue matrix were interposed between areas of cavitation. These regions were quantitatively discriminated from cavities or white matter and are collectively referred to as gray matter/matrix. In instances where tissue imperfections or processing artifacts (tears, inhomogeneity of staining, etc.) were present, data were not collected. Comparisons of morphometric data between $Cl_2MBP$-treated animals and control animals were made using unpaired t-tests or, in the case of unequal variances (F test), the Mann-Whitney nonparametric test was used. Statistical significance was set at a value of $p<0.05$.

Results

Morphometric analyses of the lesion center did not reveal differences in section area ($p=0.23$) between the $Cl_2MBP$-treated animals and control animals. Thus, treatment with liposomes containing the $Cl_2MBP$ did not affect parameters of edema or swelling that might be mediated by post-traumatic inflammation. In contrast, a significant preservation of spinal white matter at the impact site was observed in the $Cl_2MBP$-treated animals. Marked differences were also noted between the $Cl_2MBP$-treated animals and control animals when evaluating regions of cavitation. In the $Cl_2MBP$-treated rats, cavities were significantly reduced in size at the lesion site and in caudal spinal segments.

What is claimed is:

1. a method for treating a patient with a contusion-type spinal cord injury comprising
   (a) providing a patient with a contusion-type spinal cord injury, and
   (b) then administering liposomes containing dichloromethylene diphosphonate to said patient, wherein said liposomes are administered prior to onset of infiltration of the spinal cord by peripheral macrophages.

2. The method of claim 1 wherein said liposomes are administered to said patient at least once within 24 hours after occurrence of said injury.

3. The method of claim 1 wherein said liposomes are administered to said patient at least once within a period extending from 0 hours to 7 days after occurrence of said injury.

4. The method of claim 1 wherein said liposomes are administered to said patient multiple times within a period extending from 0 hours to 7 days after occurrence of said injury.

5. The method of claim 1 wherein said liposomes are first administered to said patient more than eight hours after occurrence of said injury.

6. The method of claim 1 wherein said liposomes comprise phosphatidylcholine.

7. The method of claim 5 wherein said liposomes further comprise cholesterol.

* * * * *